US009696242B2

(12) United States Patent
Walker et al.

(10) Patent No.: US 9,696,242 B2
(45) Date of Patent: Jul. 4, 2017

(54) FIXED CHAMBER SEPARATOR WITH ADJUSTMENT WITHDRAWAL MEMBER

(71) Applicant: Biomet Biologics, LLC, Warsaw, IN (US)

(72) Inventors: Trenton Walker, Warsaw, IN (US); Matthew D. Landrigan, Fort Wayne, IN (US); Michael D. Leach, Warsaw, IN (US); Scott R. King, New Orleans, LA (US); Randel Dorian, San Diego, CA (US); Richard W. Storrs, Berkeley, CA (US)

(73) Assignee: Biomet Biologics, LLC, Warsaw, IN (US)

( * ) Notice: Subject to any disclaimer, the term of this patent is extended or adjusted under 35 U.S.C. 154(b) by 0 days.

(21) Appl. No.: 14/510,619

(22) Filed: Oct. 9, 2014

(65) Prior Publication Data

US 2015/0104824 A1    Apr. 16, 2015

Related U.S. Application Data

(60) Provisional application No. 61/889,303, filed on Oct. 10, 2013.

(51) Int. Cl.
*G01N 1/18* (2006.01)
*B01L 3/00* (2006.01)
(Continued)

(52) U.S. Cl.
CPC .............. *G01N 1/18* (2013.01); *B01L 3/5021* (2013.01); *A61M 1/029* (2013.01); *A61M 1/3693* (2013.01);
(Continued)

(58) Field of Classification Search
CPC . G01N 1/18; B01L 3/5021; B01L 2400/0633; B01L 2300/046; B01L 2300/049
See application file for complete search history.

(56) References Cited

U.S. PATENT DOCUMENTS 3,879,295 A * 4/1975 Glover et al. ................ 210/516
4,059,108 A * 11/1977 Latham, Jr. ........... B04B 5/0442
494/18

(Continued)

FOREIGN PATENT DOCUMENTS

KR          101194044 B   * 10/2012
WO     WO-2008143570 A1    11/2008
WO     WO-2015054613 A1     4/2015

OTHER PUBLICATIONS

International Search Report and Written Opinion mailed Feb. 2, 2015 for PCT/US2014/060097 claiming benefit of U.S. Appl. No. 14/510,619, filed Oct. 9, 2014.

(Continued)

*Primary Examiner* — Jill Warden
*Assistant Examiner* — Matthew Krcha
(74) *Attorney, Agent, or Firm* — Schwegman Lundberg & Woessner, P.A.

(57) ABSTRACT

A separation device that can include a separation tube or container that has a wall defining an internal volume into which a material can be placed is disclosed. The material can include a multi-component mixture or solution. A secondary tube or withdrawal cannula can be placed and/or moved within the tube to withdrawal a material form the tube.

21 Claims, 10 Drawing Sheets

(51) Int. Cl.
- *G01N 1/10* (2006.01)
- *A61M 1/36* (2006.01)
- *G01N 33/49* (2006.01)
- *A61M 1/02* (2006.01)

(52) U.S. Cl.
CPC ... *B01L 2200/026* (2013.01); *B01L 2300/046* (2013.01); *B01L 2300/049* (2013.01); *B01L 2300/0858* (2013.01); *B01L 2400/0633* (2013.01); *G01N 33/491* (2013.01); *G01N 2001/1025* (2013.01)

(56) References Cited

U.S. PATENT DOCUMENTS

| | | | |
|---|---|---|---|
| 6,234,948 B1* | 5/2001 | Yavilevich | 494/20 |
| 2003/0205538 A1 | 11/2003 | Dorian et al. | |
| 2010/0120596 A1* | 5/2010 | Froman et al. | 494/8 |

OTHER PUBLICATIONS

What is PRP? Webpage, Tozai Holdings, Inc. www.prosysglobal.com (1997-2011) 5 pages.

"International Application Serial No. PCT/US2014/060097, International Preliminary Report Patentability mailed Apr. 21, 2016", 7 pgs.

"European Application Serial No. 14789714.4, Response filed Dec. 13, 2016 to Communication pursuant to Rules 161(2) and 162 EPC mailed Jun. 3, 2016", 15 pgs ..

* cited by examiner

FIXED CHAMBER SEPARATOR WITH ADJUSTMENT WITHDRAWAL MEMBER

CROSS-REFERENCE TO RELATED APPLICATIONS

This application claims benefit of U.S. Provisional Patent Application No. 61/889,303 filed on Oct. 10, 2013. The entire disclosure of the above application is incorporated herein by reference.

FIELD

The subject disclosure is related to separating materials, and particularly to separating a multi-component material including gravimetrically separable portions.

BACKGROUND

This section provides background information related to the present disclosure which is not necessarily prior art.

A material having a plurality of components or constituents can be separated into individual constituents based upon gravimetric separation, if each of the constituents includes a different specific density. For example, a particulate having a high density can be separated from an aqueous solution by applying a force to the solution. The force can be applied to the aqueous solution including the particulates by placing it in a centrifuge to apply a force greater than that of gravity. Over time, the denser materials will collect in a container near a wall that is in the direction of the force.

Once a material is separated, a selected fraction, including at least one of the components of the material in the solution or mixture, can be withdrawn from the container. When more than one component is included in the solution or mixture, access to the plurality of fractions may be difficult. Accordingly, it is desirable to provide a system that can efficiently separate and provide access to one or more of the factions of the separated material.

SUMMARY

This section provides a general summary of the disclosure, and is not a comprehensive disclosure of its full scope or all of its features.

A separation device can include a separation tube or container that has a wall defining an internal volume into which a material can be placed. The material can include a multiple component (multi-component) material that is a mixture or solution. The multi-component material can be separated using gravimetric separation. The separation can be assisted by centrifugation by placing the tube in a centrifuge device. During centrifugation, a force can be applied to the separation device that is greater than the force of gravity to cause the gravimetric separation of components within the material.

The separation tube can include an internal structure, including a surface, which enhances or allows efficient access to a plurality of the components of the separated material. For example, the separated material can include whole blood that is separated into at least a plasma fraction, a buffy coat fraction, and a red blood cell fraction. The buffy coat can be positioned between the plasma fraction and the red blood cell fraction after centrifugation. The internal structure can include a reduced or selected internal diameter that minimizes a surface area over which the buffy coat is spread. Accordingly, an efficient and high percentage extraction of the buffy coat material can be made from the whole blood separation.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1A:
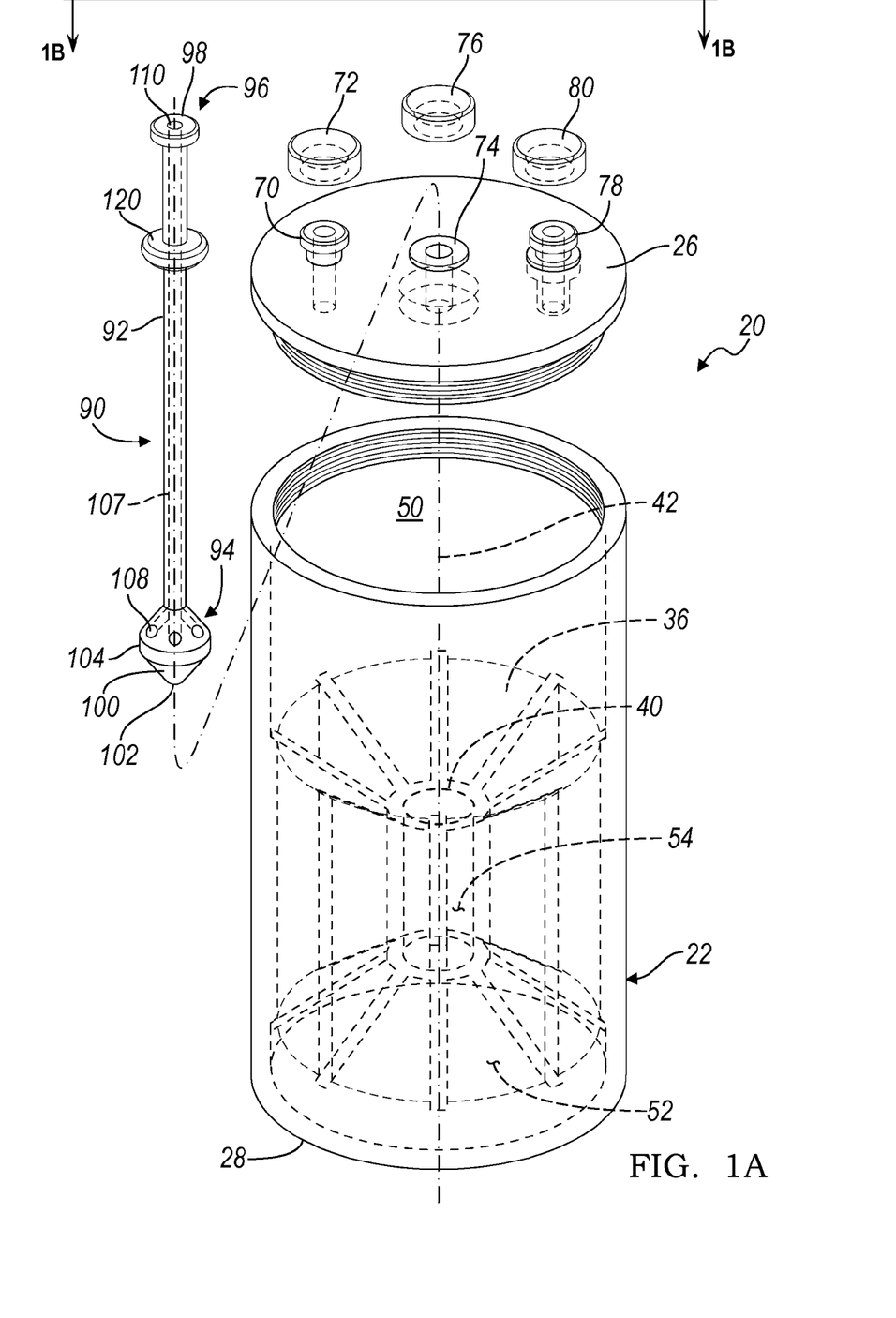
FIG. 1A is an exploded perspective view of a separation device.
Figure 1B:
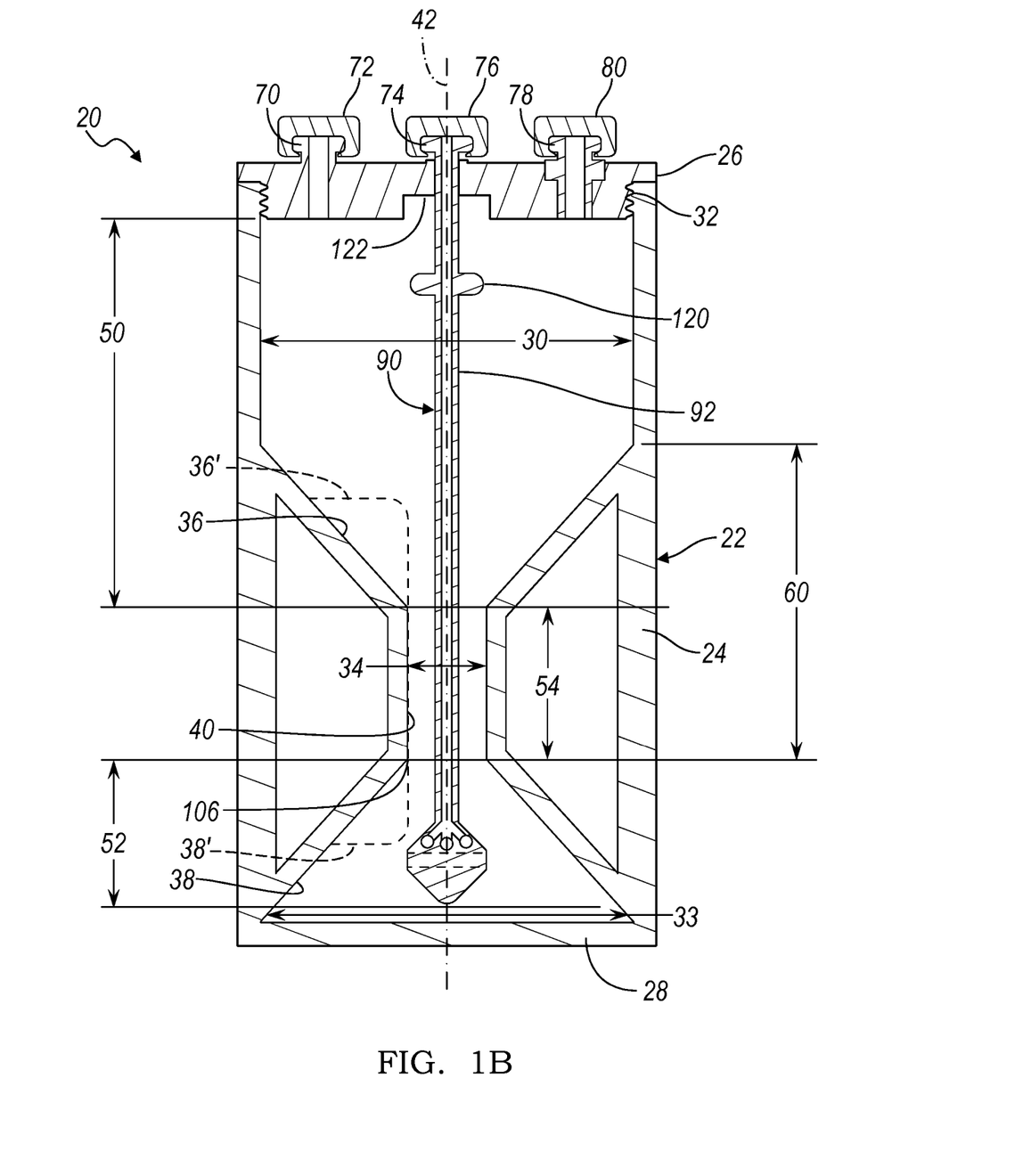
FIG. 1B is an assembled cross-section view of the device of FIG. 1A.

With reference to FIGS. 1A and 1B, a separation device 20 is illustrated. The separation device 20 can include a separation tube or container 22 that includes an external or side wall 24 that extends from a top 26 to a bottom 28. The top 26 can include a top wall that is a separate top or lid member that is placed on the container 22 or can be formed integrally therewith. Additionally, the bottom 28 can be a bottom wall that is also a separate wall or member that is positioned on the container 22 or formed integrally therewith. Accordingly, in various embodiments, the bottom wall 28 and the sidewall 24 can be formed as a single piece and the top 26 can be a cap that is positioned onto the sidewall 24. The top cap 26 can be connected and/or sealed to the sidewall 24 with a threaded or tortuous path seal. Other connections and/or seals can include a friction fit or an adhesive or other appropriate material.

The container 22 can define a first internal diameter 30 near a first end 32 of the sidewall 24 that can be near the top 26. The internal diameter 30 can be similar or identical to an internal diameter 33 defined near the bottom wall 28. The internal diameters 30 and 33 can be a large or maximum diameter of the container 22. It is understood, however, that only one of the internal diameters 30 or 33 may be a maximum diameter while the other diameter is smaller. According to various embodiments, at least the internal diameter 30 nearest the first end 32 of the container 22 will be a maximum internal diameter of the container 22.

The container 22 can define at least one second internal diameter 34 that is a minimum or minimal internal diameter. The minimum of minimal internal diameter 34 can be defined by a surface that is formed by an internal wall structure or configuration including a first conical wall section 36, a second conical wall section 38, and an intermediate wall section 40. The intermediate wall section 40 can be substantially cylindrical and extend along or be coaxial with a center axis 42 of the container 22. It is understood that the first conical wall 36, second conical wall 38, and the intermediate wall section 40 can be any appropriate shape. For example, the conical wall sections 36 and 38 can simply be flat or stacked, as illustrated in phantom lines in FIG. 1B as 36' and 38'. Accordingly, the minimal internal diameter 34 can be defined between any appropriate section of the internal or minimal wall section 40 within the container 22.

The container 22 can define a first area or volume 50 in a first section generally between the top wall 26 and at least an initial portion of the central wall section 40, a second volume 52 in a second section between the bottom wall 28 and at least a second portion of the middle wall section 40, and a third volume 54 as generally defined by at least a portion of the height or extent of the middle wall portion 40 within the container 22. The various volumes 50, 52, and 54 can be used to define areas for collection of materials as discussed further herein. It is understood, however, as also discussed further herein, that the various volumes 50, 52, and 54 can be interconnected for separation of various components. For example, operation of the separation system 20 can allow for collection of a material within a volume 60 that can be defined by at least the middle wall section 40 and a portion of the volume 50 that extends towards the top wall 26. A buffy coat component of a whole blood volume can be separated into a volume that is greater than the volume defined between the middle wall portion 40 and may extend and cover at least a portion of the conical wall 36. Accordingly, the volume of buffy coat can be greater than the volume 54 defined by the middle wall portion 40 and may include a portion of the volume 50. Accordingly, volume 60, defined by the container 22, can include the buffy coat fraction of a whole blood sample.

The separation container 22 can further include various access ports. For example, a delivery or access port 70 can be provided to deliver material into the container 22. A cap 72 can be provided to cover the access port 70. A withdrawal or access port 74 can be provided to withdraw a selected portion of the material from within the container 22 at selected locations, as discussed further herein. A cap 76 may cover the port 74. A third port 78 can also be provided, such as for venting the container 22. A cap 80 can be provided to selectively cover the port 78.

Provided within the container 22, and to selectively access fractions of a material positioned within the container 22, can be a withdrawal or aspiration member 90. The aspiration member 90 can include an elongated shaft 92 that can be dimensioned to allow for a distal or first end 94 to be positioned near the bottom wall 28 while a proximal or second end 96 can be positioned or accessed through the port 74. The second end 96 can include a stop or engagement portion 98 that engages the port 74 such that the aspiration tube 90 can be moved relative to the sidewall 24 of the container 22. The movement of the aspiration tube 90 can be substantially axially, such as limited by the cap 26.

The distal end 94 can be shaped to be positioned within the volume 52 of the container 22. For example, the distal end 94 can include a first section 100 that can include a terminal end 102 to engage or be positioned to contact the end wall 28 of the container 22. A sealing portion 104, which can be a contacts portion that is centrally located on the distal end 94, can be dimensioned to engage an edge 106 of the conical wall 38. The waist or contact surface 104, however, can also be dimensioned to engage any appropriate portion of the internal dimension of the container 22, including a portion of the central or middle wall portion 40.

As discussed further herein, the contact waist portion 104 can provide a seal between the end wall 28 and a volume within the container between the waist portion 104 and the top wall 26. Generally, the seal is formed between the volume 52 and the remainder of the volume of the container 22. Further, the seal formed may liquid tight or be formed to minimize or not allow movement of liquid from the volume 52 during withdrawal through the withdrawal member 90. Accordingly, material can be aspirated through the withdrawal member 90 that is in a volume above or between the top wall 26 and the waist portion 104 while sealing this volume from the remainder of the container 22. Thus, the material can be withdrawn without aspirating or mixing with a material that is between the sealing portion 104 and the end wall 28.

The aspiration member 90 can further include an aspiration cannula or passage 107 that can interconnect with one or more aspiration ports 108 and a terminal or withdrawal port 110. The aspiration ports 108 can provide access to a volume within the container 22 to allow for withdrawal of material from within the container 22. A selected withdrawal system, such as a syringe, can interconnect with the flange 98 to sealingly engage with the aspiration tube 90 to aspirate or withdraw material through the aspiration passage 107 and through the aspiration terminus 110 of the aspiration member 90.

The aspiration member 90 can further include a stop or engagement ledge 120. The stop 120 can provide a physical barrier to movement of the aspiration member 90 within the container 22. For example, the stop 120 can engage a surface, such as a bottom surface 122 of the top wall 26 of the container 22. Accordingly, the stop 120 can limit movement of the aspiration member 90 within the container 22, as discussed further herein.

Figure 2:
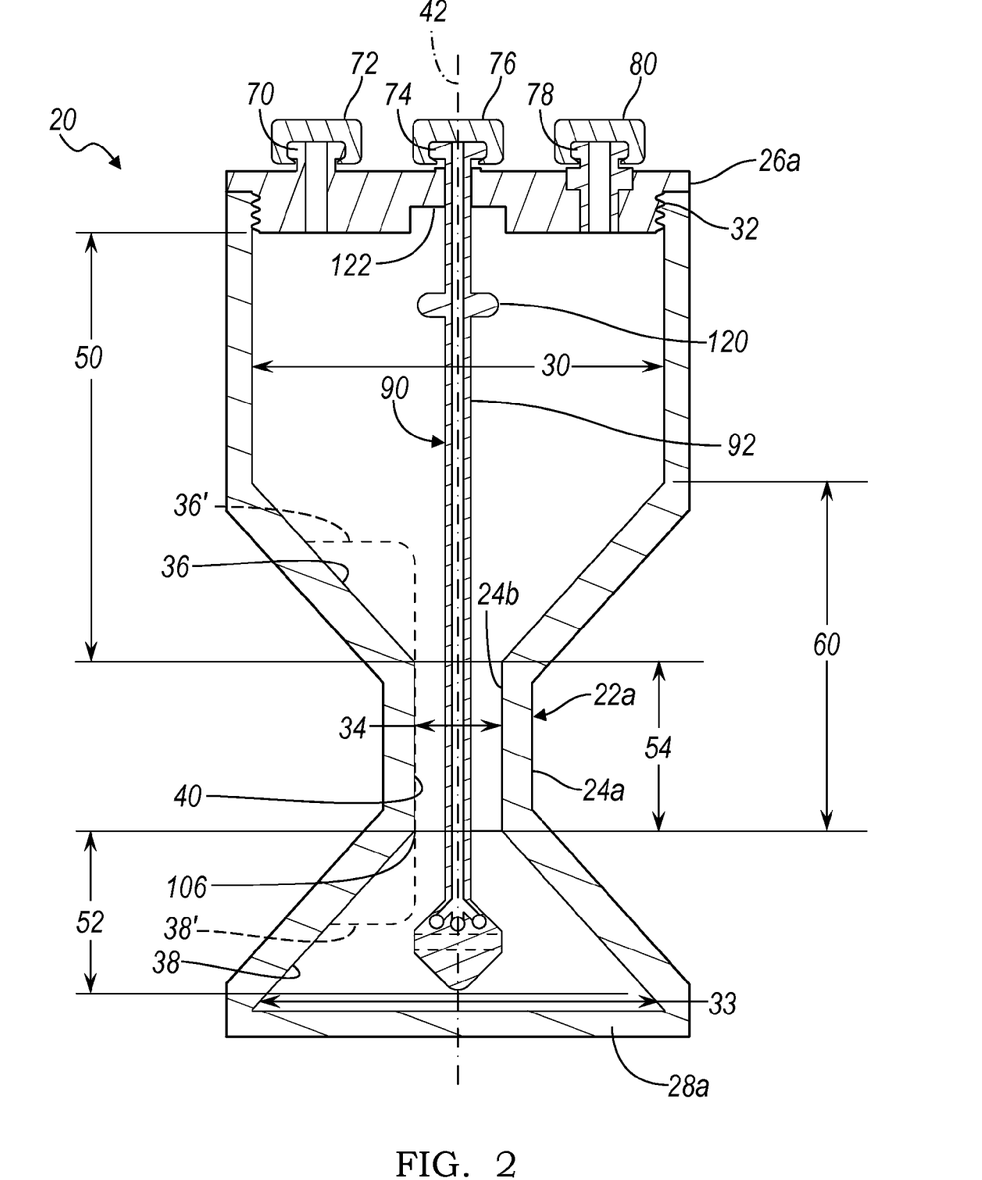
FIG. 2 is an assembled cross-section view of a device, according to various embodiments.

With reference to FIG. 2, the separation system 20 can be formed with a container 22a. The container 22a may be similar to the container 22 discussed above and include an external or side wall 24a that extends from a top 26a to a bottom 28a, similar to those discussed above. The container 22a can define the first internal diameter 30 near the first end 32 of the sidewall 24 that can be near the top 26a. The internal diameter 30 can be similar or identical to the internal diameter 32 defined near the bottom wall 28a. The internal diameters 30 and 32 can be similar or identical to those discussed above regarding the container 22.

The container 22a can define the at least one second internal diameter 34 that is a minimum or minimal internal diameter. The minimum of minimal internal diameter 34 can be defined by a surface 24b of the sidewall 24a. As illustrated in FIG. 2, the sidewall 24a can extend internally or taper towards the central axis 42 of the container 22a to define the small diameter 34. The sidewall 24a, at other portions, can extend substantially straight to define a cylinder or cylindrical shape.

The sidewall 24a, therefore, can form the an internal wall structure or configuration including the first conical wall section 36, the second conical wall section 38, and the intermediate wall section 40. The intermediate wall section 40 can also be substantially cylindrical and extend along or be coaxial with the center axis 42 of the container 22a. It is understood that the first conical wall 36, second conical wall 38, and the intermediate wall section 40 can be any appropriate shape.

Figure 3:
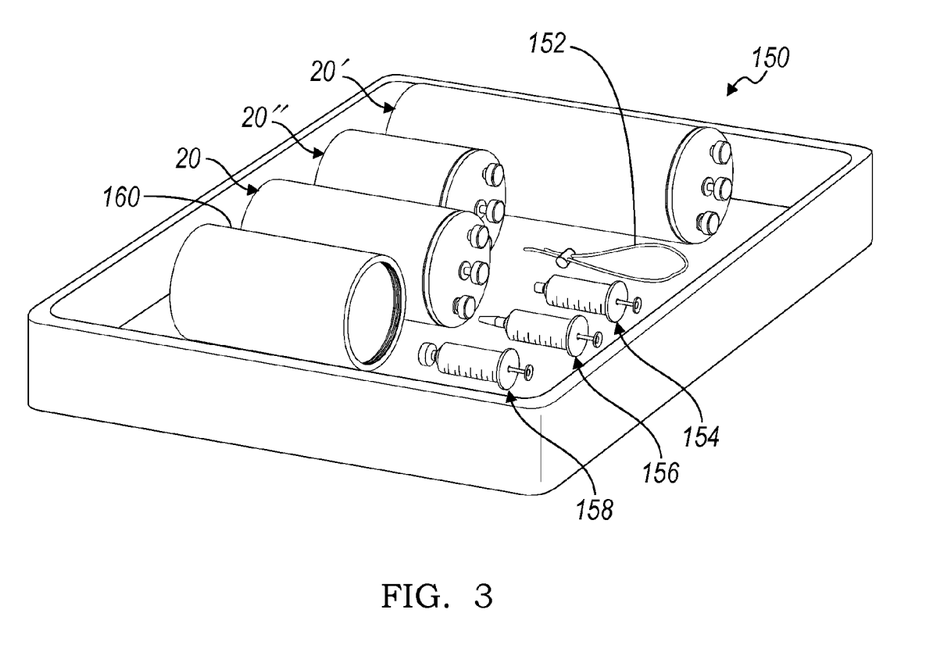
FIG. 3 is a kit of a separation device system, including possible multiple sizes.

With reference to FIG. 3, the separation system 20 can be provided in a kit 150. The kit 150 can include separation systems 20' and 20" that can vary in internal volumes and external sizes. Also or alternatively, several kits can be provided for selection including a single separation system of different sizes, including internal volumes sizes that differ.

The kit 150 can also include various other components such as a tourniquet 152 to assist in the withdrawal of blood from a subject, such as a human patient. A withdrawal or delivery system, including a syringe 154 can also be provided. The withdrawal syringe 154 can include various additional substances, such as an anti-coagulating agent. One or more withdrawal systems can also be provided, such as a first withdrawal syringe 156 and a second withdrawal syringe 158. As discussed further herein, the separation system 20 can allow for separation of more than one component from a multi-component material. Accordingly, the various or plurality withdrawal systems 156 and 158 can be used to separately withdraw selected components from the separation system 20. The kit 150 can also include a second separation system 20 and/or a counter balance 160 that could be used to counter balance a centrifuge, as discussed further herein. For example, a volume of saline or other liquid can be used to fill the counter balance 160 with a volume equivalent to the volume placed in the separation system 20.

Figure 4:
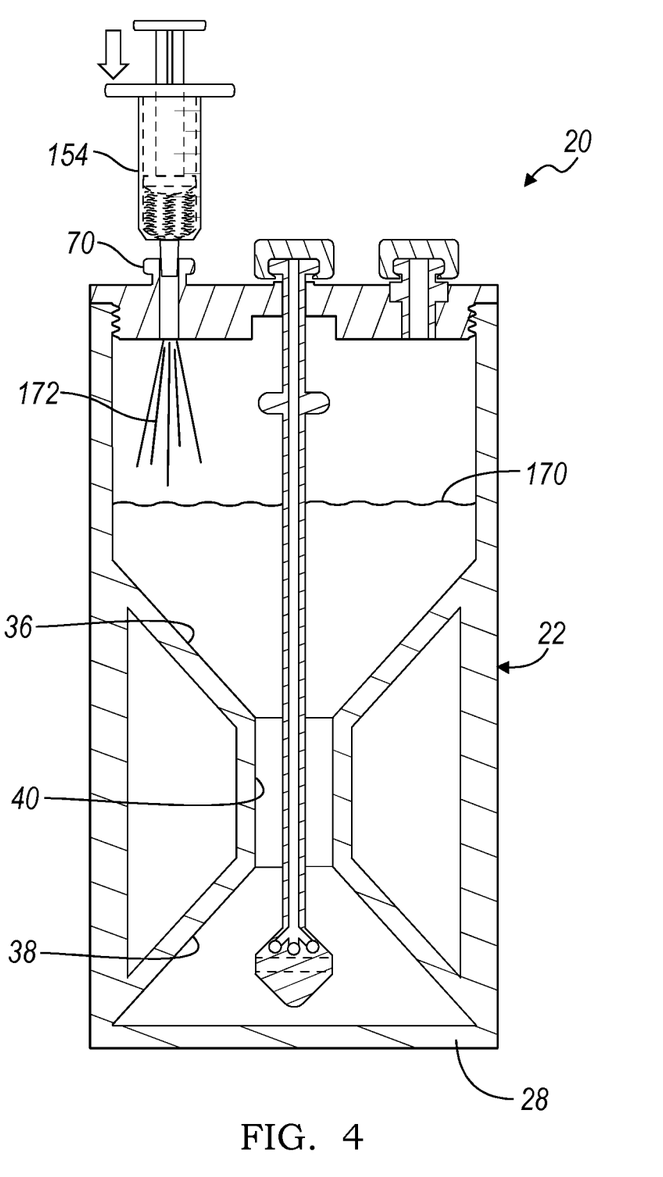
FIG. 4 is an assembled cross-section view of the device of FIG. 1A being filled.

According to various embodiments, the separation system 20 can be filled with a selected volume of a multi-component material, such as whole blood, from the introduction syringe 154, as illustrated in FIG. 4. The introduction syringe 154 can be used to withdraw a whole blood sample that can also be referred to as an introduction volume, from a selected subject. The whole blood sample or a selected volume thereof can be introduced into the separation system 20. A selected volume of whole blood 170 can be introduced into the container 22 through the introduction port 70, as illustrated by the introduction of a multicomponent material 172.

Once the selected volume of material is placed within the separation container 22, the introduction syringe 154 can be removed from the separation system 20. The selected volume of material positioned within the separation container 20 can be selected or based upon an available amount of materials to be withdrawn from the selected subject. As discussed further herein, it is understood that a smaller subject may be able to provide only a limited volume of material. For example, an adult human subject may be able to provide a volume of whole blood substantially equivalent to about 60 milliliters (ml). A juvenile human patient, a canine subject, or other non-human subject may be able to provide only a limited volume, such as less than 60 ml of material. In certain instances as little as 2-10 ml, including about 5 ml can be introduced into the separation system 20. As further discussed herein and illustrated in FIG. 3, the separation system 20 can also be customized or provided in various sizes. The separation system 20 can be selected based on the withdrawn or available material. In the various sizes of the separation system 20, the selected volumes or sections 50, 52, 54, and 60 can be customized and/or selected based upon the provided or accessible volume of whole blood or whole material. A user can select the size of the separation system 20 based on the application, experience, available volume of whole material, etc. Generally, the volumes or sections 50, 52, 54, and 60 are fixed or predetermined in the various sized separation systems 20.

Figure 5:
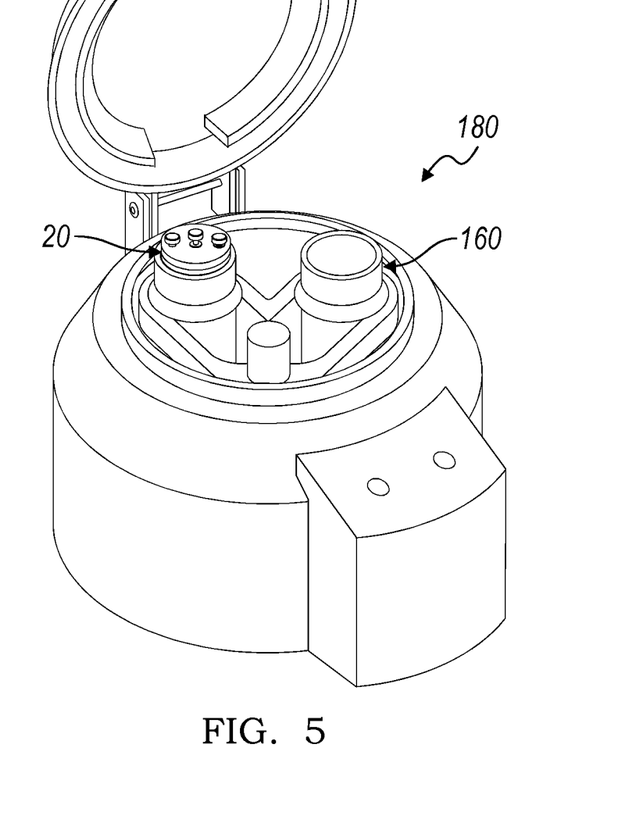
FIG. 5 is an environmental view of a separation device in a centrifuge.

Nevertheless, according to various embodiments, once the selected volume of whole material 170 is positioned within the separation system 20, the separation system 20 can be positioned in a centrifuge 180, as illustrated in FIG. 5. The filled separation container 20 can be positioned within the centrifuge 180 opposite the counter balance 160. The counter balance 160, as discussed above, can be filled with a selected volume of material to substantially balance the centrifuge 180, as is generally understood in the art. The centrifuge 180 can then be operated for a selected period of time at a selected spin rate or velocity to gravimetrically separate the components of the whole material, such as whole blood, placed within the separation system 20. It is understood that the speed and time can be varied within the centrifuge 180 to achieve a selected separation. For example, an entire spin time can be a single selected velocity to have the various components of the whole material separated at the single velocity. Furthermore, the spin rate can vary over time to achieve a selected separation. Moreover, a different spin time or velocity can be selected based upon a volume of the whole material positioned within the separation container. According to various embodiments the separation system 20 can be spun at a velocity of about 1,000 rotations per minute (RPM) to about 8,000 RPMs, including about 1,000 RPMs to about 5,000 RPMs for a time of about five (5) minutes to about 40 minutes, including about 5 minutes to about fifteen (15) minutes. According to various embodiments, the separation system 20 can include a volume of about 60 ml of whole blood which can be spun at a velocity of about 5,000 RPMs for about 5 minutes. It is understood that the spin rate and time may be varied. For example, the sample may be spun at a rate of 2,000 RPMS for two minutes, then spun at a rate of 5,000 RPMs for about 3 minutes.

Figure 6:
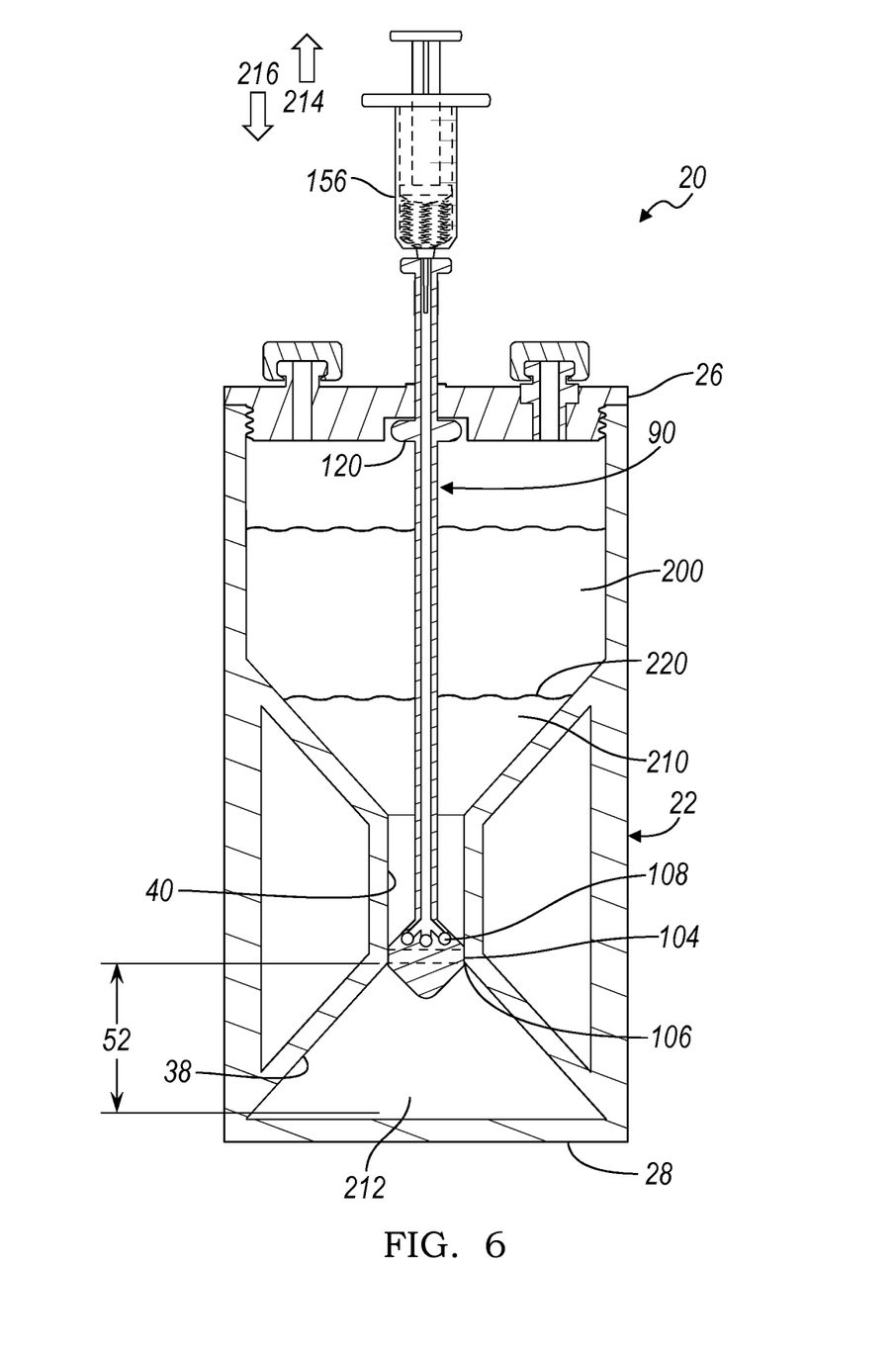
FIG. 6 is an assembled cross-section view of the device of FIG. 1A with a material separated therein.

With reference to FIG. 6, after the spin in the centrifuge 180 the whole blood sample can be separated into a plurality of components in various fractions. For example, a plasma fraction 200 can be positioned between the top 26 and a middle or second fraction 210. The middle or second fraction 210 can include a buffy coat fraction that can include various components, such as at least a portion of white blood cells and/or platelets of the whole blood sample. A third fraction 212 can include the densest components of the whole blood sample, such as red blood cells and erythrocytes. The separate fractions within the container 22 can be accessed with the aspiration member 90 by moving the aspiration member 90 away from the bottom wall 28 generally in the direction of arrow 214 and/or moving the aspiration member 90 towards the bottom wall 28 generally in the direction of arrow 216.

According to various embodiments, the buffy coat or middle fraction 210 can be visually distinguished from the red blood cell fraction 212 and the plasma fraction 200. Generally, the red blood cell fraction 212 is dark red and opaque. The plasma fraction 200 is substantially clearer or yellowish and substantially transparent. The buffy coat fraction 210 can be darker than the plasma fraction 200 and only partially transparent or translucent. Accordingly, a withdrawal of the buffy coat fraction 210 can be made by moving the aspiration tube 90 to a selected position within the container 22, such as so that the stop 120 engages the cap or top wall 26 and the waist or sealed section 104 engages the contact surface 106 of the internal diameter. The first withdrawal container 156 can engage the aspiration tube 90 and withdraw the buffy coat fraction 210 into the first to withdrawal container 156.

By visual inspection, the withdrawal of the buffy coat 210 can be viewed as the interface 220 between the plasma fraction 200 and the buffy coat fraction 210 moves towards the aspiration ports 108 of the aspiration tube 90. Once the interface 220 reaches the aspiration ports 108, a visual determination that an extraction or withdrawal of the entire buffy coat 210 from the container 22 has been made. Generally, the position of the contact point 106 and the internal volume of the volume 52 can be designed to allow for a minimal or small withdrawal of red blood cells such as about 0.01 ml to about 1.0 ml can be made. By allowing a small extraction of red blood cells, the withdrawal of the buffy coat fraction 210 can be assisted in assuring that substantially the entire buffy coat 210 is withdrawn from the whole blood sample.

Further, the position of the ports 108 allows for withdrawal of the fraction that is between the seal section 104 and the top 26 of the container 22. Thus, one of more of the lighter separates fractions can be withdrawn without accessing of the heavier fractions. This allows efficient removal of the lighter fractions by a single user and/or a single spin of the container 22.

The distal end 94 of the withdrawal member 90 can be moved internally within the container 22 to the contact portion 106. The withdrawal member 90 can be moved from a location exterior to the container, as illustrated in FIG. 6, the distal end 94 may remain within the container 22 during an entire separation and withdrawal operation.

Figure 7:
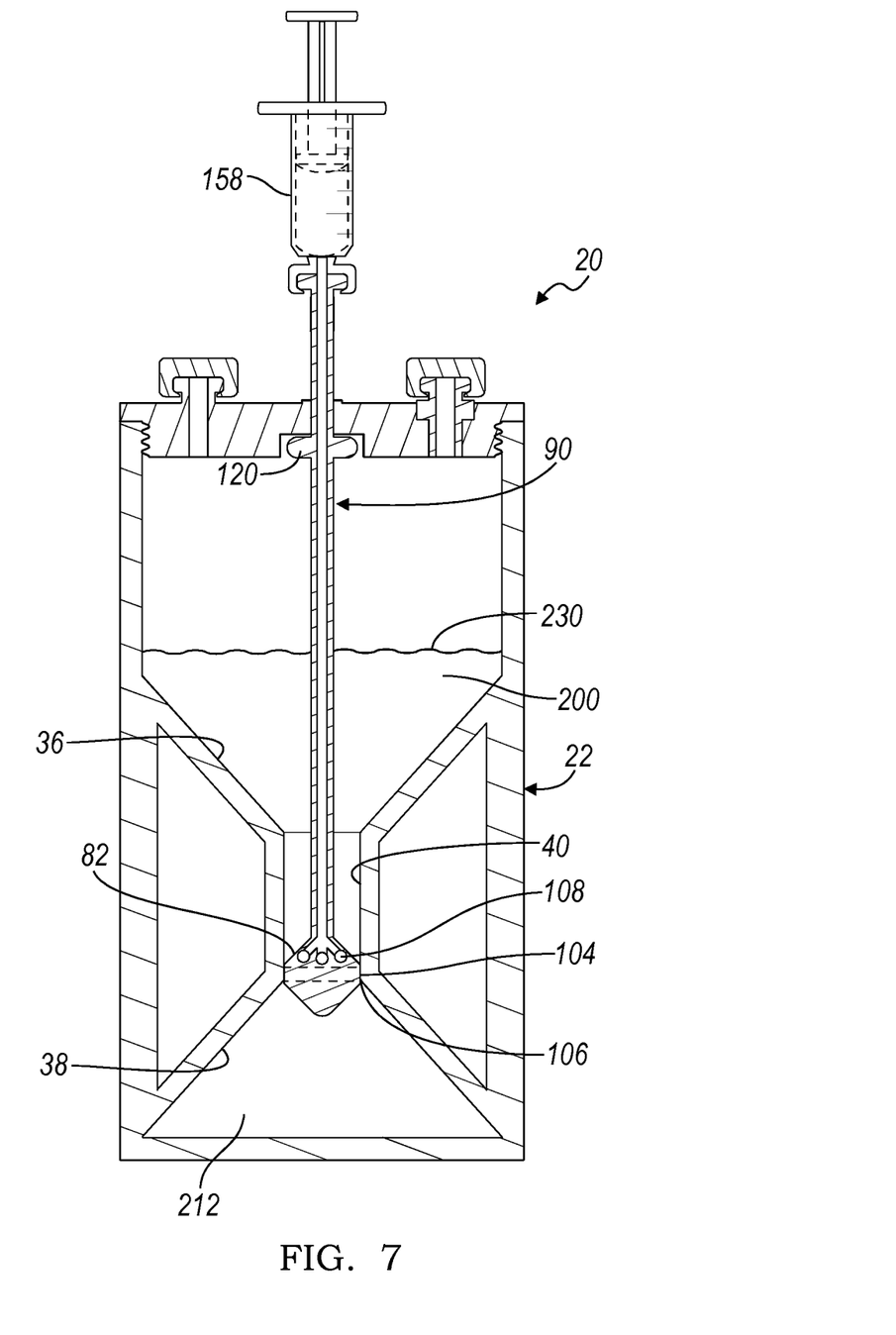
FIG. 7 is an assembled cross-section view of the device of FIG. 1A with a material separated therein and a partial extraction from the device.

After the buffy coat 210 has been withdrawn from the container 22, and with reference to FIG. 6, the container 22 will substantially then contain only the plasma fraction 200 and the red blood cell fraction 212. The second withdrawal container 158 can then be interconnected with the aspiration member 90. After the connection, the withdrawal container 158 can withdraw the plasma fraction 200 through the aspiration ports 108. Again, the contact of the sealing region 104 with the contact portion 106 can seal the plasma fraction 200 from the red blood cell fraction 212. The withdrawal of the plasma fraction 200 can also be visually identified by viewing a movement of a top surface of the plasma fraction 230 towards an interface 232 between the plasma fraction and the red blood cell fraction. When the top of the plasma fraction 230 substantially reaches the red blood cell interface 232, a visual indication that the entire plasma fraction 200 has been withdrawn can be made. Additionally, after withdrawal of the buffy coat 210, generally the aspiration ports 108 are only contacting or in access with the plasma fraction 200. Thus, the plasma fraction 200 can be withdrawn separately and completely from the buffy coat 210.

Figure 8:
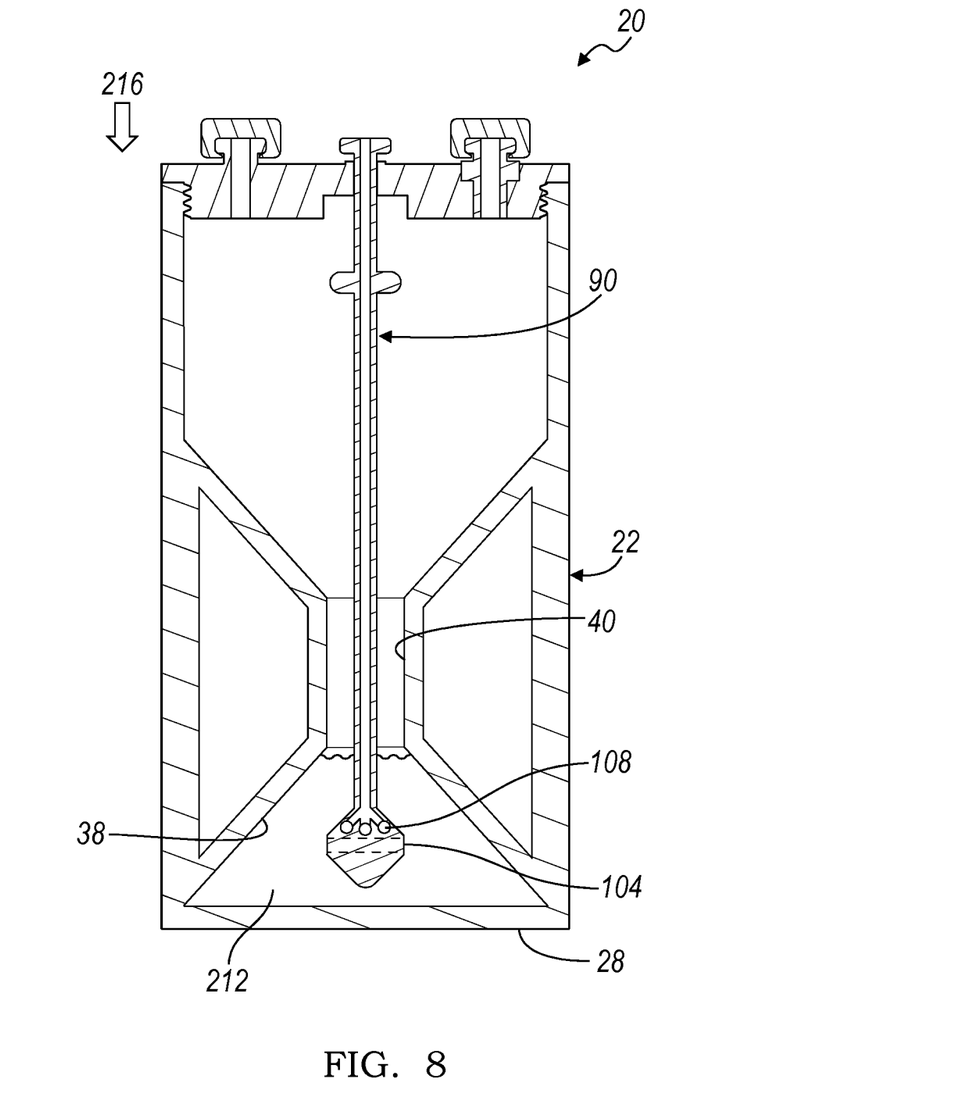
FIG. 8 is an assembled cross-section view of the device of FIG. 1A with a material separated therein and a partial extraction from the device.

With reference to FIG. 8, if desired, the red blood cell fraction 212 can be withdrawn from the container 22 by moving the aspiration member 90 in the direction of arrow 216 to generally contact or position the aspiration member 90 in contact with the bottom wall 28. Thus, the aspiration ports 108 will be immersed within the red blood cell fraction 212 and at least a selected portion of the red blood cell fraction 212 can be withdrawn. It is understood that a third withdrawal container can be used to withdraw the red blood cell fraction 212 and/or the red blood cell fraction can be mixed with another fraction withdrawn from the container 22 or an empty withdrawal container can be used to withdraw the red blood fraction. Regardless, the aspiration member 90 can allow for withdrawal of a plurality of fractions of material, such as fraction of a whole blood sample, from within the container 22 without requiring additional components, such as a buoy or a float.

The whole blood sample positioned within the separation system 20 can be substantially gravimetrically separated and the different components identified substantially visually. The various volumes of the container 22, such as the volume 50, 52, and 54, can be designed, formed, and/or used to selectively withdrawal only selected fractions. The design, formation, and/or use of the volumes of the container 22 can be based upon a probable or selected volume of material positioned within the separation system 20.

For example, the bottom volume 52 can be designed based upon a known or an experimentally determined height of densely packed material, such as red blood cells. Accordingly, by providing the volume 52 at a known amount, the separation of other components above the red blood cell fraction 212 can be made. That is, it can be determined that the red blood cells from a given volume of whole blood will generally have a determined and then known volume which is equal to a height (i.e. distance of the interface) from the bottom of the container 22.

Further, by providing a minimal cross-section dimension, such as defining an internal diameter, by the middle wall 40 the cross-sectional area defined by a middle fraction can be substantially minimized. The small cross-sectional area and/or diameter allows for ease and efficiency of access and withdrawal of a selected fraction, such as a middle fraction including a buffy coat, from the separation system 20. Accordingly, the bottom volume of the container 22 can be designed based upon a selected volume of material or component of a material being positioned within the separation system 20. For example, the bottom volume can be about 0.1 ml to about 20 ml, including about 5 ml, 10 ml, 15 ml, or 20 ml.

Figure 9:
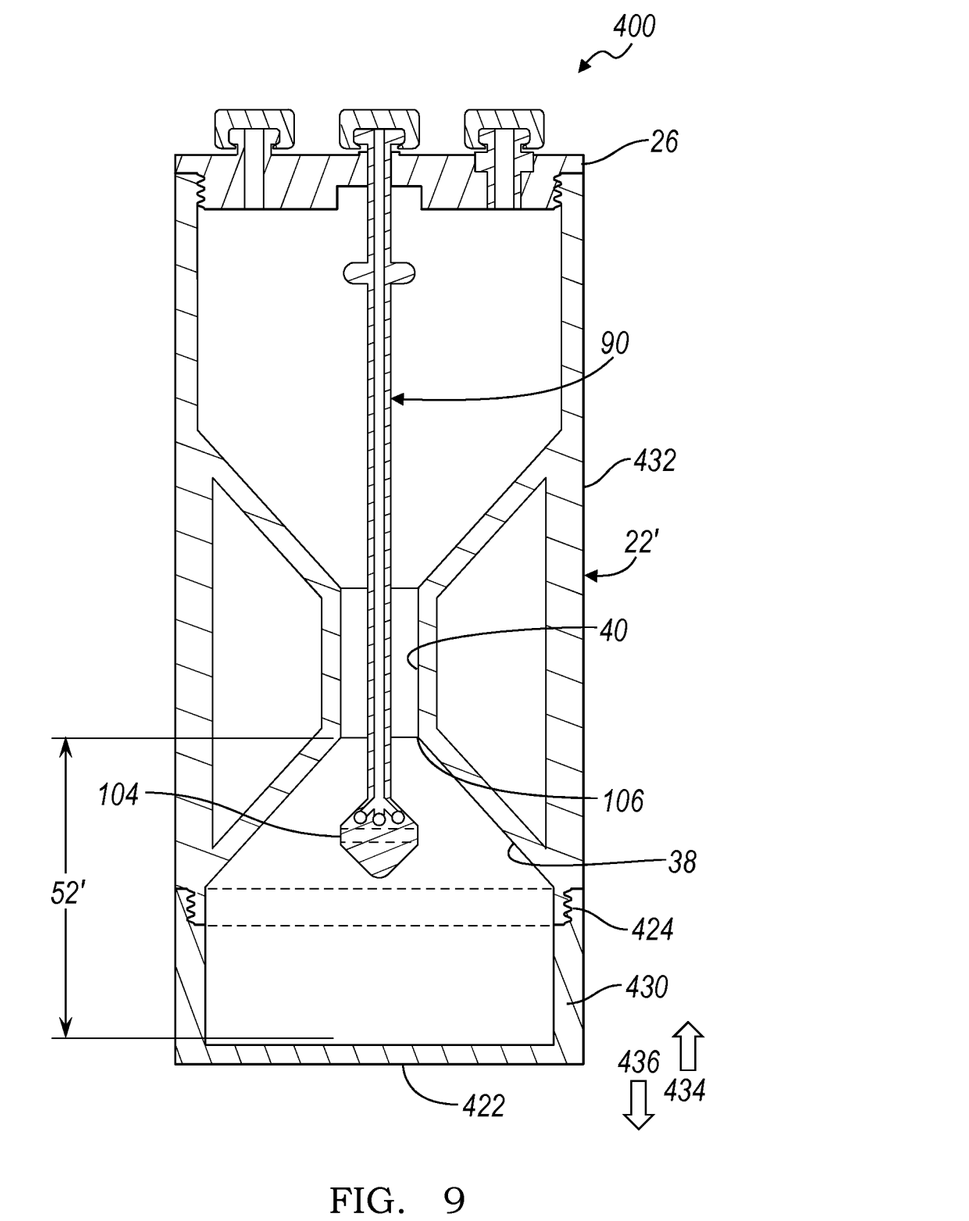
FIG. 9 is an assembled cross-section view of a separation device, according to various embodiments.

Additionally, it is understood, that the bottom volume 52 can be adjustable. With reference to FIG. 9, a separation system 400 is illustrated. The separation system 400 can be substantially identical to the separation system 20 discussed above. A bottom wall 422, however, of the separation system 400 can be removable relative to the top wall 26 through various mechanisms. Connection of the bottom wall 422 can be with a threaded engagement at a threaded region 424 between a movable bottom section 430 and an upper side wall 432 (similar to the sidewall 24 discussed above).

The threads at the threaded region 424, or other appropriate connection, can allow the bottom wall 422 to move in the direction of an arrow 434 towards the top wall 26 or the direction of an arrow 436 away from the top wall or cap 26. Due to the connection, a volume 52' can vary based upon the position of the bottom wall 422 relative to the top wall 26 and/or the contact point 106. Thus, a single separation system 400 can be provided with a selectable or alterable volume 52 such that the single separation system 400 can be used based upon selected subject in a plurality of separation systems need not provided to be selected for various subjects. As discussed above, the volume 52 can be selected to hold all or a substantial or selected portion of one or more denser fractions (e.g. red blood cells of whole blood). Thus, the other volumes of the container 22 need not be altered to allow for withdrawal of the selected lighter fractions. The operation of the separation system 400 can be substantially identical to that discussed above, save for a determination by a user of a desired or selected fraction 52' and adjusting the bottom section 430 to position the bottom wall 432 to achieve the selected bottom fraction.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system to access at least one component of a multiple component material, comprising:
    a separation container configured to receive the multiple component material including a sidewall extending from an open first end to a closed second end, the sidewall having an internal surface;
    a first internal extension wall portion extending towards a central axis of the separation container dividing the separation container into a first section at the open first end of the sidewall and a second section at the closed second end of the sidewall; and
    a withdrawal member including an elongated shaft extending from aproximal portion to a distal portion, the distal portion having a sealing portion, the withdrawal member being insertable through the open first end and moveable within the separation container relative to the first internal extension wall portion between:
        a first position in which the sealing portion is positioned to engage the first internal extension wall portion to assist in selectively removing at least one component of the multiple component material from the first section of the separation container, the distal portion having at least one port oriented for removing the at least one component of the multiple component material from the first section when the withdrawal member is positioned in the first position, and
        a second position in which the sealing portion is disengaged from the first internal extension wall portion and the distal portion of the withdrawal member is positioned within the second section to access a second component at the second section, wherein the elongated shaft having a reduced diameter to permit fluid connection between the open first end the second closed end past the first internal extension wall portion when the distal portion is positioned in the second section.

2. The system of claim 1, wherein the first internal extension wall portion is angled towards the closed second end of the separation container.

3. The system of claim 1, wherein the first internal extension wall portion includes a first section and a second section, wherein the first section is angled at a first angle towards the closed second end and the second section is angled at a second angle towards the open first end of the container.

4. The system of claim 3, wherein the withdrawal member includes:
    an elongated portion having a withdrawal bore formed therethrough, the at least one port formed through the distal portion being in fluid communication with the withdrawal bore;
    wherein the sealing portion includes an exterior surface to interact with at least one of the first section or the second section of the first internal extension wall to limit withdrawal of a selected component of the multiple component material.

5. The system of claim 4, wherein the distal portion incudes a sealing section and a tapering section;
    wherein the tapering section tapers from the sealing section towards the elongated portion.

6. The system of claim 5, wherein the at least one port in the distal portion is formed through the tapering section.

7. The system of claim 1, wherein the separation container defines at least three sections including the first section between the open first end and the first internal extension wall, the second section near the first internal extension wall portion between the first internal extension wall portion and the closed second end, and a third section between the first internal extension wall portion and the closed second end.

8. The system of claim 7, further comprising:
    a second internal extension wall portion extends towards the central axis of the separation container, wherein the second internal extension wall portion is separated from the first internal extension wall portion and nearer the closed second end than the first internal extension wall portion;
    wherein the third section is between the second internal extension wall portion and the closed second end.

9. The system of claim 8, wherein the second section is between the first internal extension wall portion and the second internal extension wall portion.

10. The system of claim 8, wherein the withdrawal member includes a sealing portion;
    wherein the sealing portion of the withdrawal member is moveable relative to the first internal extension wall portion and the second internal extension wall portion to allow for withdrawal of a selected component of the multiple component material from the separation container.

11. The system of claim 8, wherein at least one of:
    the first internal extension wall portion is a first extension member that extends from the internal surface towards the central axis of the separation container, or the second internal extension wall portion is a second extension member that extends from the internal surface towards the central axis of the separation container.

12. The system of claim 1, further comprising:
    at least one withdrawal port in communication with the withdrawal member; and
    at least one filling port separate from the withdrawal port.

13. The system of claim 1, wherein the closed second end is moveable relative to the open first end to alter a volume between the closed second end and the first internal extension wall within the separation container.

14. The system of claim 1, further comprising:
    a cap engageable to the sidewall of the separation container at e open first end to enclose the separation container;
    wherein the withdrawal member further comprises a stop positioned on the elongated shaft and configured to engage a bottom surface of the cap limiting movement of the withdrawal member toward the first end of the separation container.

15. A system to access at least one component of a multiple component material, comprising:
    a separation container configured to receive the multiple component material including a sidewall extending from an open first end to a closed second end, the sidewall having an internal surface;

a first surface portion extending towards a central ax ls of the separation container configured to define at least a first section at the open first end and a second section at the closed second end within the separation container;

a withdrawal member insertable through the open first end and having an elongated portion having a connection portion configured to extend through the open first end of the separation container and moveable to engage a sealing portion to at least a portion of the first surface in a sealing position to seal the first section from the second section such that at least a portion of the multiple component material is able to be withdrawn from only the first section through the elongated passage when the sealing portion is in the sealing position;

wherein the withdrawal member defines an elongated passage through the elongated portion that is in fluid communication with at least one of the first section and the second section;

wherein the elongated portion having a reduced diameter to permit fluid connection between the first section and the second section past the first surface portion when the sealing portion is in the second section;

wherein the withdrawal member is movable to a non-sealing position to withdrawal at least a portion of the multiple component material from the second section.

16. The system of claim 15, wherein the withdrawal member defines a withdrawal port through at least a portion of the withdrawal member positioned away from the sealing portion, wherein the withdrawal port is moveable from the first section to the second section.

17. The system of claim 15, wherein the withdrawal member is moveable relative to the first section and the second section from a position exterior to the separation container.

18. The system of claim 15, further comprising:
a withdrawal port formed through the open first end of the container;
wherein the withdrawal member extends through the withdrawal port.

19. The system of claim 15, further comprising:
a second surface extending towards a central axis of the separation container, wherein the second section is between the second surface and the closed second end of the separation container.

20. The system of claim 19, wherein at least one of:
the first surface portion extends from the internal surface of the sidewall, or the second surface portion extends from the internal surface of the sidewall.

21. The system of claim 15, further comprising:
a cap engageable to the sidewall of the separation container at the open first end to enclose the separation container;
wherein the withdrawal member further comprises a stop positioned on the elongated portion and configured to engage a bottom surface of the cap limiting movement of the withdrawal member toward the first end of the separation container.

* * * * *

UNITED STATES PATENT AND TRADEMARK OFFICE
CERTIFICATE OF CORRECTION

PATENT NO. : 9,696,242 B2
APPLICATION NO. : 14/510619
DATED : July 4, 2017
INVENTOR(S) : Walker et al.

Page 1 of 1

It is certified that error appears in the above-identified patent and that said Letters Patent is hereby corrected as shown below:

In the Claims

In Column 9, Line 28, in Claim 1, delete "aproximal" and insert --a proximal-- therefor In Column 9, Line 50, in Claim 1, after "end", insert --and--

In Column 10, Line 7, in Claim 5, delete "incudes" and insert --includes-- therefor In Column 10, Line 57, in Claim 14, delete "at e" and insert --at the-- therefor In Column 11, Line 3, in Claim 15, delete "ax Is" and insert --axis-- therefor Signed and Sealed this
Twelfth Day of June, 2018

Andrei Iancu
*Director of the United States Patent and Trademark Office*